(12) United States Patent
Ganjianpour

(10) Patent No.: US 6,716,250 B2
(45) Date of Patent: Apr. 6, 2004

(54) MODULAR FEMORAL PROSTHESIS

(76) Inventor: Ramin Ganjianpour, 17768 Alonzo Pl., Encino, CA (US) 91316

( * ) Notice: Subject to any disclaimer, the term of this patent is extended or adjusted under 35 U.S.C. 154(b) by 130 days.

(21) Appl. No.: 10/006,844

(22) Filed: Nov. 5, 2001

(65) Prior Publication Data

US 2003/0088316 A1 May 8, 2003

(51) Int. Cl.⁷ ................ A61F 2/32; A61F 2/36
(52) U.S. Cl. ................ 623/22.42; 623/22.46; 623/23.21
(58) Field of Search ............ 623/22.42, 22.43, 623/22.44, 22.45, 22.46, 23.15, 23.21, 23.22, 23.14

(56) References Cited

U.S. PATENT DOCUMENTS

| | | | |
|---|---|---|---|
| 4,995,883 A | * | 2/1991 | Demane et al. ............... 623/23 |
| 5,370,706 A | | 12/1994 | Bolesky et al. |
| 5,507,830 A | | 4/1996 | DeMane et al. |
| 5,507,833 A | | 4/1996 | Bohn |
| 5,549,706 A | | 8/1996 | McCarthy |
| 5,569,255 A | | 10/1996 | Burke |
| 5,645,607 A | | 7/1997 | Hickey |
| 5,653,764 A | * | 8/1997 | Murphy ....................... 623/23 |
| 5,653,765 A | * | 8/1997 | McTighe et al. .............. 623/23 |
| 5,702,479 A | * | 12/1997 | Schawalder .................. 623/23 |
| 5,702,480 A | | 12/1997 | Kropf et al. |
| 5,725,594 A | | 3/1998 | McTighe et al. |
| 5,876,459 A | | 3/1999 | Powell |
| 6,136,035 A | | 10/2000 | Lob et al. |
| 6,207,218 B1 | * | 3/2001 | Layrolle et al. ........... 427/2.27 |
| 6,238,436 B1 | | 5/2001 | Lob et al. |
| 6,355,068 B1 | * | 3/2002 | Doubler et al. .......... 623/22.42 |
| 6,383,226 B1 | * | 5/2002 | Carter et al. ............. 623/23.21 |
| 6,419,491 B1 | * | 7/2002 | Ricci et al. ................. 433/173 |

* cited by examiner

Primary Examiner—Eduardo C. Robert
Assistant Examiner—Anuradha Ramana
(74) Attorney, Agent, or Firm—Michael I. Kroll

(57) ABSTRACT

Disclosed is a modular femoral prosthesis having a neck element 18 that can be selectively positioned atop a stem element 12 by inserting a grooved shaft 26 that extends downward from the bottom of the neck element 18 into a corresponding slotted recess 32 originating on a top portion of the stem element 12 and continuing longitudinally partially therethrough. The axial orientation of the neck element 18 relative to the stem element 12 can thus be rotated accordingly during insertion of the grooved shaft 26 into the slotted recess 32. The stem 13 can be cylindrical in form or tapered. Locking screw 30 is provided to secure the neck element 18 to the stem element 12.

9 Claims, 11 Drawing Sheets

MODULAR FEMORAL PROSTHESIS

BACKGROUND OF THE INVENTION

1. Field of the Invention

The present invention relates generally to femoral prosthetic devices and, more specifically to a modular femoral prosthesis having a neck element that can be selectively positioned atop a stem element by inserting a grooved shaft that extends downward from the bottom of said neck element into a corresponding slotted recess originating on a top portion of the stem element and continuing longitudinally partially therethrough. The axial orientation of the neck element relative to the stem element can thus be rotated accordingly during insertion of the grooved shaft into the slotted recess. The stem can be cylindrical in form or tapered.

The size and the amount of grooves in the shaft and the corresponding slots in the recess predetermine the rotational variance from one position to the next, preferably in increments of 5–10 degrees per position to allow for the proper adjustment needed for a particular patient.

In addition, neck elements with varying lengths and offsets are provided to accommodate the needs of individual patients and to work in concert with the selectively rotated neck element to afford the orthopedic surgeon with a versatile modular femoral prosthetic. The surface of the stem portion can be gritblast or porous coated for press fit insertion in which the prosthesis is maintained in place by bone that grows into the porous surface or could be smooth for cementation applications. The modular characteristics of the stem element which becomes integral with the femur whether press fit or cemented and the removable neck element that is removably screwed thereto gives the orthopedic surgeon greater flexibility when a revision is necessary. Furthermore, the rotative capabilities of the neck element upon insertion or reinsertion could preclude the necessity of replacing or removing the stem element from the femur to adjust the angle to the needs of the patient during such a revision.

2. Description of the Prior Art

There are other modular femoral prosthetic devices. Typical of these is U.S. Pat. No. 5,370,706 issued to Richard Bolensky et al. on Dec. 6, 1994 and U.S. Pat. No. 5,507,830 was issued on Apr. 16, 1996 to Michael DeMane et al. On Apr. 16, 1996 Bohn was issued U.S. Pat. Nos. 5,507,833 and 5,549,706 was issued to McCarthy on Aug. 27, 1996.

Another patent was issued to Burke on Oct. 29, 1996 as U.S. Pat. No. 5,569,255. Yet another U.S. Pat. No. 5,645,607 was issued to Hickey on Jul. 8, 1997 and still yet another was issued on Aug. 5, 1997 to McTighe et al. as U.S. Pat. No. 5,653,765.

U.S. Pat. No. 5,702,480 was issued to Kropf et al. On Dec. 30, 1997 and a patent was issued to McTighe et al. on Mar. 10, 1998 as U.S. Pat. No. 5,725,594. Yet another U.S. Pat. No. 5,876,459 was issued to Powell on Mar. 2 1999. Another was issued to Lob et al. on Oct. 24, 2000 as U.S. Pat. No. 6,136,035 and still yet another was issued to Lob et al. on May 29, 2001 as U.S. Pat. No. 6,238,436.

U.S. Pat. No. 5,370,706

Inventor: Richard Bolesky et al.

Issued: Dec. 6, 1994

A modular hip prosthesis for the replacement of a portion of the femur is provided. The prosthesis is assembled from a kit that includes a stem member having an upper portion and a lower portion, with the lower portion sized to be received in the femur. The kit also includes a body member that is sized to replace a portion of the femur and is configured to be received over the upper portion of a stem member. The kit also includes a head member that is sized to replace the head of the femur. A neck member is provided to attach the head member to the body member to form an assembled prosthesis.

U.S. Pat. No. 5,507,830

Inventor: Michael Demane et al.

Issued: Apr. 16, 1996

A modular hip prosthesis can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. The tubular extension sleeve has an open end portion receptive of the lower tapering stem of the prosthesis body. The stem portion includes an internal bore, and an attachment in the form of an elongated screw is provided for connection to the stem internal bore for securing the extension sleeve and the prosthesis body together, forming a compressive sealed connection therebetween. Pads can be attached to the transitional mid-section of the prosthesis body for increasing the cross-sectional shape of the prosthesis at the transitional mid-section. The pads are loaded continuously to connect to the prosthesis body by the hip joint reaction force. Removable collars can be added to the prosthesis to form a transverse load carrying interface with the upper end of the patient's femur. Frustroconically-shaped extension sleeves can be added to the prosthesis neck for extending the neck length.

U.S. Pat. No. 5,507,833

Inventor: William W. Bohn

Issued: Apr. 16, 1996

A joint replacement system particularly useful in total hip arthroplasty includes a prosthesis presenting a macrotextured dimpled surface thereon for promoting biological fixation of the prosthesis to the surrounding bone. The prosthesis may be, for example, a femoral prosthesis, which is designed for insertion along the intramedullary canal of a bone. The femoral prosthesis presents a body portion having a cruciform cross-section and a distal portion which is wide in the coronal plane for conforming to the endosteum of the bone but narrow in the sagittal plane for provide good flexure with the bone. The femoral prosthesis is configured to leave a portion of the intramedullary canal undisturbed to provide better circulation to the bone-growth regions after surgery. The prosthesis may also be an acetabular component having the macrotextured outer surface which permits the shell-like acetabular component to be thinner and also to avoid the necessity of pins or screws ordinarily required to attach an acetabular component to the acetabulum of the pelvis. The invention further includes a novel method of implanting the prosthesis which includes leaving a portion of the intramedullary canal intact rather than reaming out the intramedullary canal to receive the prosthesis as is conventional.

U.S. Pat. No. 5,549,706

Inventor: Thomas F. McCarthy

Issued: Aug. 27, 1996

A femoral hip prosthesis comprises a main member, a modular member and a means for connecting the two. The main member has a stem portion and a body portion which are adapted for insertion into the intramedullary canal. The body portion has lateral, posterior, and anterior sides adapted to mate with the bone and has a medial side configured and dimensioned to receive a modular member. The modular member is chosen from a plurality of such members of various shapes and sizes and is adapted to fit accurately into the intramedullary canal, especially after the intramedullary canal has been deformed through the prior implantation of a prosthetic hip device.

U.S. Pat. No. 5,569,255

Inventor: Dennis W. Burke

Issued: Oct. 29, 1996

A prosthetic device for the human hip having elongated fins or other like protrusions which are provided on the underside of a collar and which extend into previously formed slots or grooves in the bone. Either a plurality of fins, or a single fin having a non-rectilinear shape is provided. Apparatus for formation of the grooves in the bone includes a mill guide which can be mounted onto the proximal end of a rasp embedded in a cavity formed in the bone. A milling bit is used in conjunction with the mill guide to form precisely located and shaped grooves into which the fins can seat. A clamp is provided for securing the prosthetic device to the femur while the cement is hardening.

U.S. Pat. No. 5,645,607

Inventor: Paul Francis Hickey

Issued: Jul. 8, 1997

A hip stem provisional 10 having adjustable neck offsets is disclosed. Hip stem provisional 10 includes a stem part 12 and an attachable cone provisional 20. Cone provisional 20 includes a base 30 and a neck 40 shiftably connected to the base. Base 30 has a mounting surface 36 upon which neck 40 is shiftably seated. Neck 40 can be positioned along the length of mounting surface 36 at a plurality of discrete positions. In one embodiment of cone provisional 20, base 30 has an arcuate mounting surface 36, which allows neck 40 to be positioned along the length of the mounting surface at a plurality of discrete positions, each having a different neck offset and neck angle. In a second embodiment of the cone provisional 60, the base 70 has a flat mounting surface 76, which allows the neck 80 to be positioned along the length of the mounting surface at a plurality of discrete positions, each having a different neck offset, but having a fixed neck angle.

U.S. Pat. No. 5,653,765

Inventor: Timothy McTighe et al.

Issued: Aug. 5, 1997

A modular hip stem prosthesis including a separate and interchangeable stem piece and proximal shoulder piece. Coronal and sagittal slots are formed in a rounded distal end of the stem in a substantially right-angle orientation. A neck member extends angularly outward from the shoulder piece and is configured to receive a spherical hip ball for insertion into the hip socket. The proximal shoulder piece includes a cylindrical projection for insertion into an axial bore formed in an upper end of the stem. An annular lip is formed in side walls defining the axial bore, and a distal end of the cylindrical projection abuts the lip when it is inserted into the bore. Radial teeth are formed on a distal end of the cylindrical projection and mate with compatible teeth formed on the annular lip to thereby render the shoulder piece removably mountable onto the stem. A locking screw securely joins the shoulder piece with the stem. The stem piece can be unitary or made up of a separate and interchangeable distal stem piece and metaphyseal component. The shoulder piece is selectable from an array of shoulder pieces having various heights and lengths to thereby provide spacing in two dimensions between the femur and the pelvis which reduces the risk of hip dislocation without introducing the problems of leg elongation and femur splintering.

U.S. Pat. No. 5,702,480

Inventor: Philipp Rolf Kropf et al.

Issued: Dec. 30, 1997

The modular hip prosthesis has an axial stem forming its distal part. Two modular proximal parts can be mounted on the stem from its proximal end and be rigidly connected thereto. Because the prosthesis has two modular parts at its proximal end, it can be optimally adapted to match the bone geometry intraoperatively. The diameter of the prosthesis in its proximal part and the position of the hip joint can be defined independently. Due to its slim shape and a drain for medullary material, the stem can directly be driven into the bone and does not require a pre-drilled cavity.

U.S. Pat. No. 5,725,594

Inventor: Timothy McTighe et al.

Issued: Mar. 10, 1998

A cementless femoral hip stem component includes an elongate stem having opposing distal and proximal sections. The proximal section includes a conical stem surface which terminates in a proximal end. A collar having a conical undersurface extends laterally outward from the proximal end of the stem. The proximal conical stem portion and the conical undersurface of the collar cooperatively define a unitary double-cone contact surface to allow the collar to subsidably engage with external cortical bone in tandem with the proximal conical stem subsidably engaging with the internal femoral canal.

U.S. Pat. No. 5,876,459

Inventor: Douglas Hunter Powell

Issued: Mar. 2, 1999

An implantable modular orthopedic prosthesis, preferably for hip or knee arthroplasty, is disclosed which consists of three components. A first component has an elongated stem with a free end, configured to be situated within the intramedullary canal of a patient's bone, and an opposite end having an articulating portion such as a Morse-tapered member. A second component has another articulating portion which can also be a corresponding Morse-tapered member that is matingly engageable with the articulating portion of the first component. A third component has a body with a linearly-extruded channel through which the articulating portions are adjustably received, wherein at least one of the components is radially-expansible to pressure lock against an internal surface of the channel in a selected position and arrest the first, second and third components together as the articulating portions are fully engaged with one another. The present modular orthopedic implant functions as a unitary biomechanical structure and is easy to use, as it is interoperatively adjustable to fit minute variations in a patient's given anatomy, while minimizing the inventory of component sizes needed on hand during surgery.

U.S. Pat. No. 6,136,035

Inventor: Gunter Lob et al.

Issued: Oct. 24, 2000

A modular hip joint prosthesis is assembled from a head section having a connection for the ball of the joint and from a shaft section. The shaft section is joined by a insert connection to the head section, and provision is made for fixing the insert connection. The insert connection is situated in the region of Shenton's arc. The respective contours, in longitudinal section, of the head and shaft sections in the region of the connection merge smoothly, without any substantial change in direction, irrespective of the relative mutual alignments of the sections at any given time, with the exception of a gap in the immediate vicinity of the connection.

U.S. Pat. No. 6,238,436 B1

Inventor: Gunter Lob et al

Issued: May. 29, 2001

A modular artificial hip joint includes a head part and at least one shaft part. The shaft part, which can be driven into the bone and forms the distal region, is connected to the distal end of the head part by insertion, preferably by means of an insert cone. A first screw or tie rod, guided through an axial bore in the head part, can be screwed into the threaded bore in the shaft part. In order to guide a second screw for separating the conical insert connection between the individual components of the artificial joint, the bore in the head part is threaded and has a diameter which is greater than the diameter of the threaded bore in the shank part.

While these femoral prosthetic devices may be suitable for the purposes for which they were designed, they would not be as suitable for the purposes of the present invention, as hereinafter described.

SUMMARY OF THE PRESENT INVENTION

The present invention discloses a modular femoral prosthesis having a neck element that can be selectively positioned atop a stem element by inserting a grooved shaft that extends downward from the bottom of the neck element into a corresponding slotted recess originating on a top portion of the stem element and continuing longitudinally partially therethrough. The axial orientation of the neck element relative to the stem element can thus be rotated accordingly during insertion of the grooved shaft into the slotted recess. The stem can be cylindrical in form or tapered. A locking screw is provided to secure the neck element to the stem element. The size and the amount of grooves in the shaft and the corresponding slots in the recess predetermine the rotational variance from one position to the next, preferably in increments of 5–10 degrees per position to allow for the proper adjustment needed for a particular patient.

A primary object of the present invention is to provide a modular femoral prosthesis that will allow a surgeon to adjust the angle, the offset and the length of the neck to accommodate the needs of each patient.

Still another object of the present invention is to provide a modular femoral prosthesis having a neck element compatible with conventional synthetic femoral heads used with modular femoral components and the artificial sockets that replace the cup-shaped bone of the pelvis called the acetabulum that form the ball and socket joint.

Yet another object of the present invention is to provide a modular femoral prosthesis wherein the neck element is available having the neck in various offsets and lengths.

Still yet another object of the present invention is to provide a modular femoral prosthesis wherein the neck element is secured in place longitudinally by a locking screw passing through a central recess in the grooved shaft and into a threaded recess.

Another object of the present invention is to provide a modular femoral prosthesis wherein the stem element has a biocompatible surface that could be gritblast or porous coated for press fit applications or smooth for cementation.

Another object of the present invention is to provide a modular femoral prosthesis having a neck element and a stem element wherein the neck element has a gear-like grooved shaft that is inserted into a corresponding slotted recess in the stem element in which the axial rotation and/or version of the neck element is selectively determined upon insertion therein.

Yet another object of the present invention is to provide a modular femoral prosthesis that is economical in cost to manufacture.

Additional objects of the present invention will appear as the description proceeds.

The present invention overcomes the shortcomings of the prior art by providing a modular femoral prosthesis that provides the orthopedic surgeon with a versatile means of making multiple adjustments regarding the axial orientation, offset angle and length of the neck to meet the considerations of each individual patient and different implantation applications.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
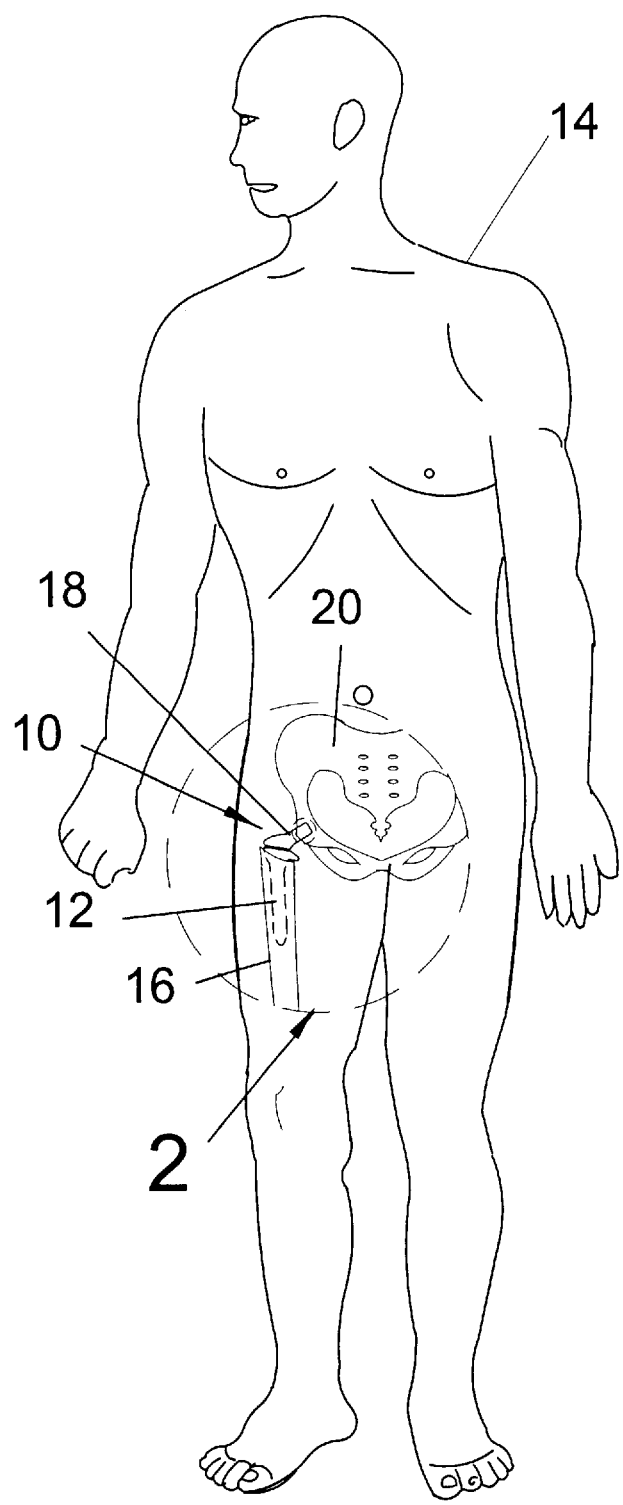
FIG. 1 is an illustrative view of the present invention in use.

With regard to reference numerals used, the following numbering is used throughout the drawings.

10 present invention
12 stem element
13 stem
14 patient
16 femur
18 neck element
19 neck
20 pelvis
22 femoral ball
24 artificial socket
26 grooved shaft
28 leg
30 locking screw
32 slotted recess
34 central recess
36 threaded recess
38 collar
40 tapered stem element
41 tapered stem
42 tapered shaft
44 thicker neck element
46 thicker neck
48 locking means

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Turning to FIG. 1, shown therein is the present invention 10, a two piece modular femoral prosthesis comprising an elongated stem element 12 that is placed longitudinally inside the patient's 14 femur 16 and a neck element 18 having a grooved shaft that is in inserted into the stem element 12 and a neck element 18 that inserts into a conventional synthetic femoral head that rotates within an artificial acetabulum. The neck element 18 could be rotated to an appropriate position relative to the stem element 12 prior to insertion therein. The pelvis 20 is also shown.

Figure 2:
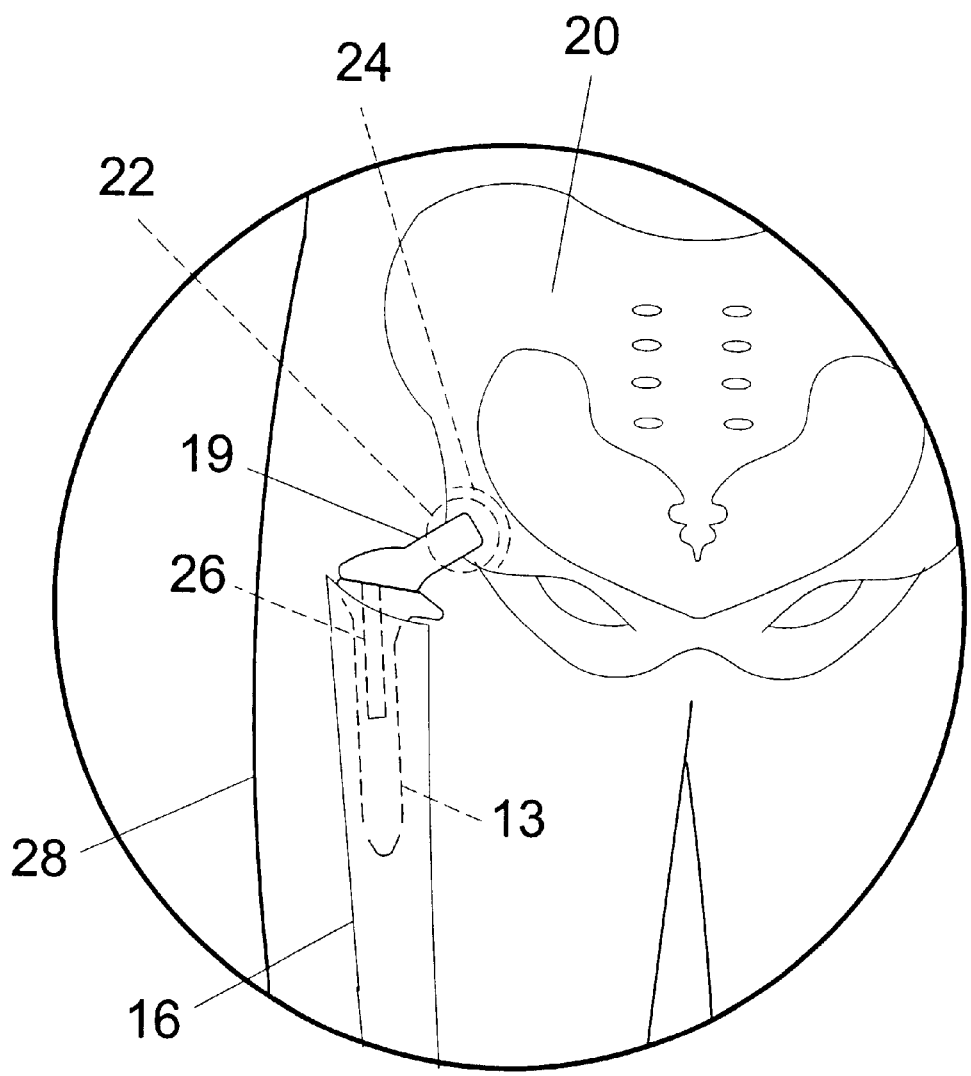
FIG. 2 is a detailed illustrated view of the present invention taken from FIG. 1 as indicated.

Turning to FIG. 2, shown therein is the stem 13 inserted into the femur 16 of the patient and a femoral ball 22 connected to the neck 19 where it rotates within an artificial socket 24. Also shown is a grooved shaft 26 inserted longitudinally internal the stem element 12 along with leg 18 and pelvis 20 of the patient.

Figure 3:
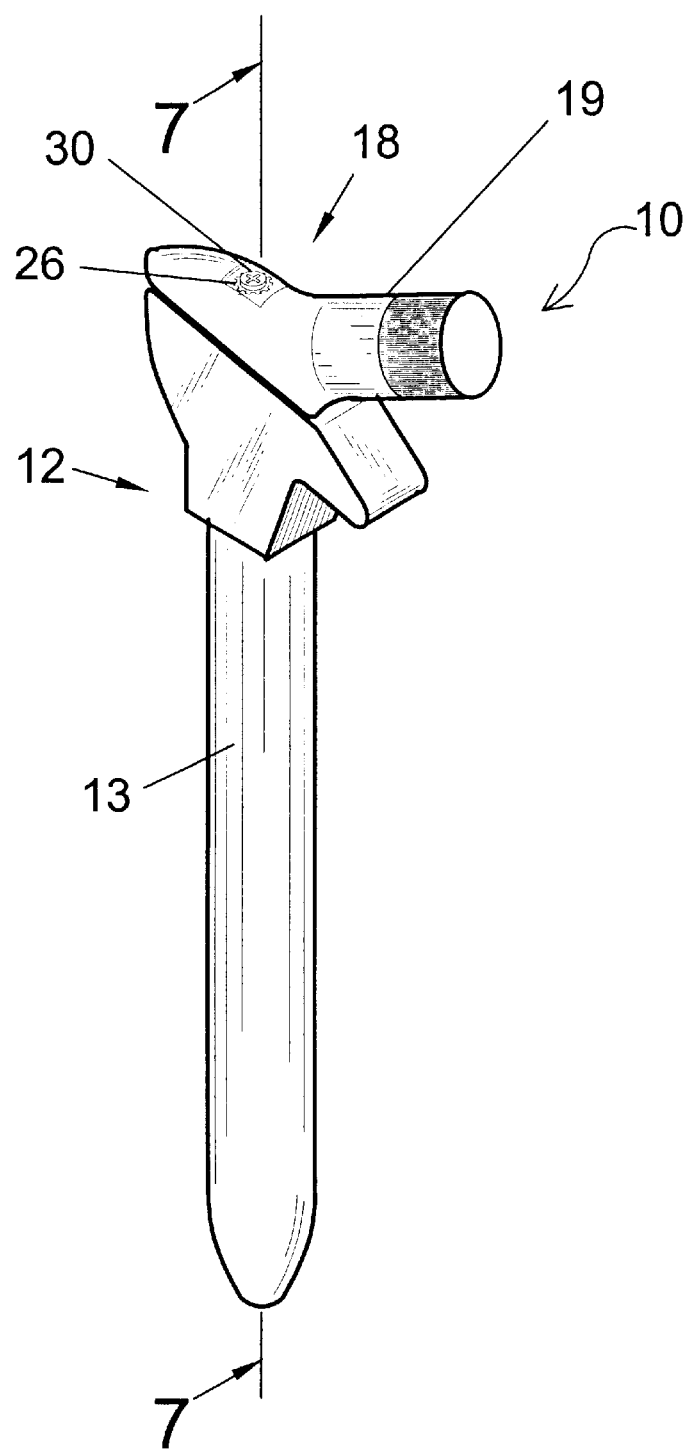
FIG. 3 is a perspective view of the present invention.

Turning to FIG. 3, shown therein is the present invention 10 wherein a neck 19 with the proper offset and length has been selected and installed in the stem element 12 in alignment therewith. However, the axial rotation of the neck element 18 relative to the stem element 12 could be achieved by rotating the neck element 18 to the desired position prior to insertion. The present invention is particularly helpful when adjustments are needed after the stem 13 has already been cemented or during revisions when the removal of the stem 13 from the femur would otherwise be unnecessary. Also shown are the grooved shaft 26 and a locking screw 30.

Figure 4:
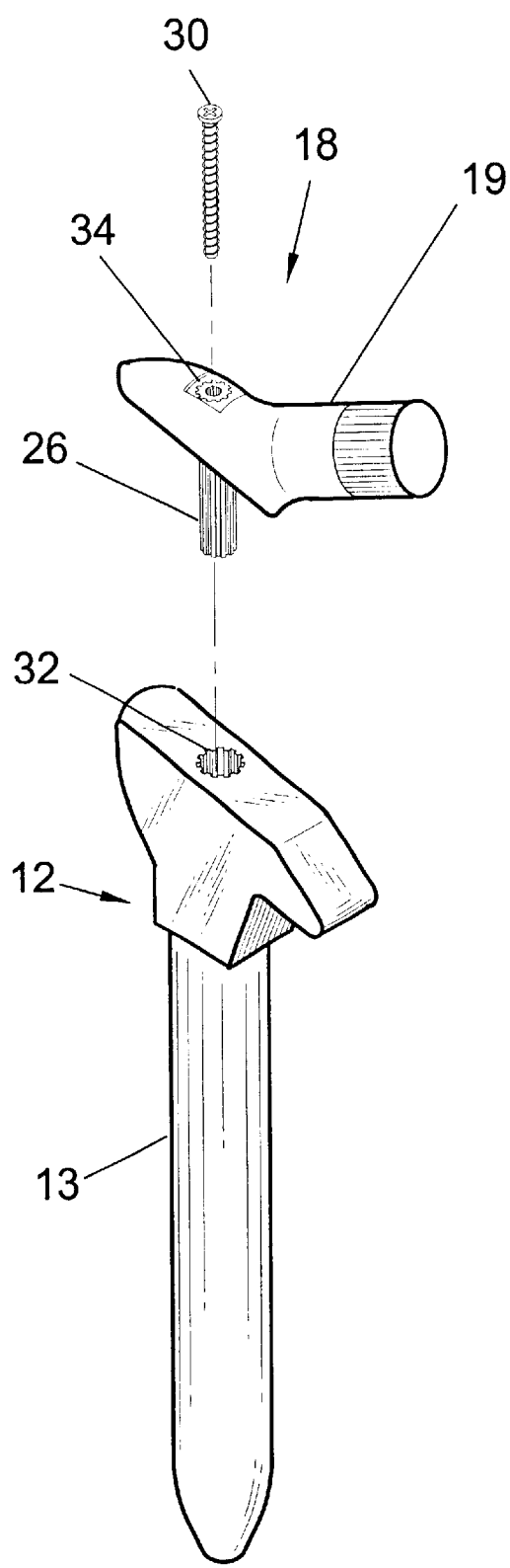
FIG. 4 is an exploded perspective view of the present invention.

Turning to FIG. 4, shown therein is the neck element 18 rotated to the desired position upon installation and the grooved shaft 26 inserted into the slotted recess 32 with the interlocking respective slots and grooves prohibiting rotational movement thereof. The locking screw 30 is placed into a central recess 34 extending longitudinally through the entire length of the grooved shaft 26 and thereafter screwed into the threaded recess (not shown but see FIG. 7) at the lower end of the slotted recess 32 to prevent the vertical movement thereof. The size and the amount of grooves in the shaft 26 and the corresponding slots in the recess 32 predetermine the rotational variance from one position to the next, preferably in increments of 5–10 degrees per position to allow for the proper adjustment needed for a particular patient. Other elements previously disclosed are also shown.

Figure 5:
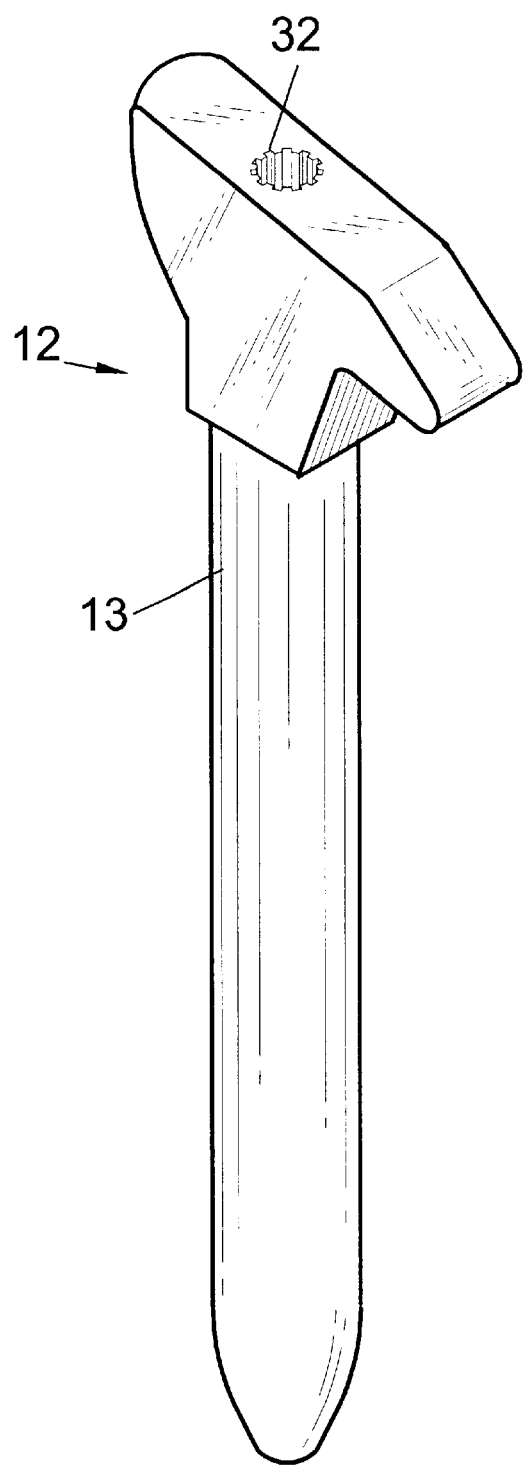
FIG. 5 is a perspective view of the stem element.

Turning to FIG. 5, shown therein is the gear-like structure of the slotted recess 32. The stem 13 of the stem assembly element 12 is inserted into the femur of the patient and the neck is fastened to a femoral ball that rotates within an artificial acetabulum to simulate a natural ball and socket joint.

Figure 6:
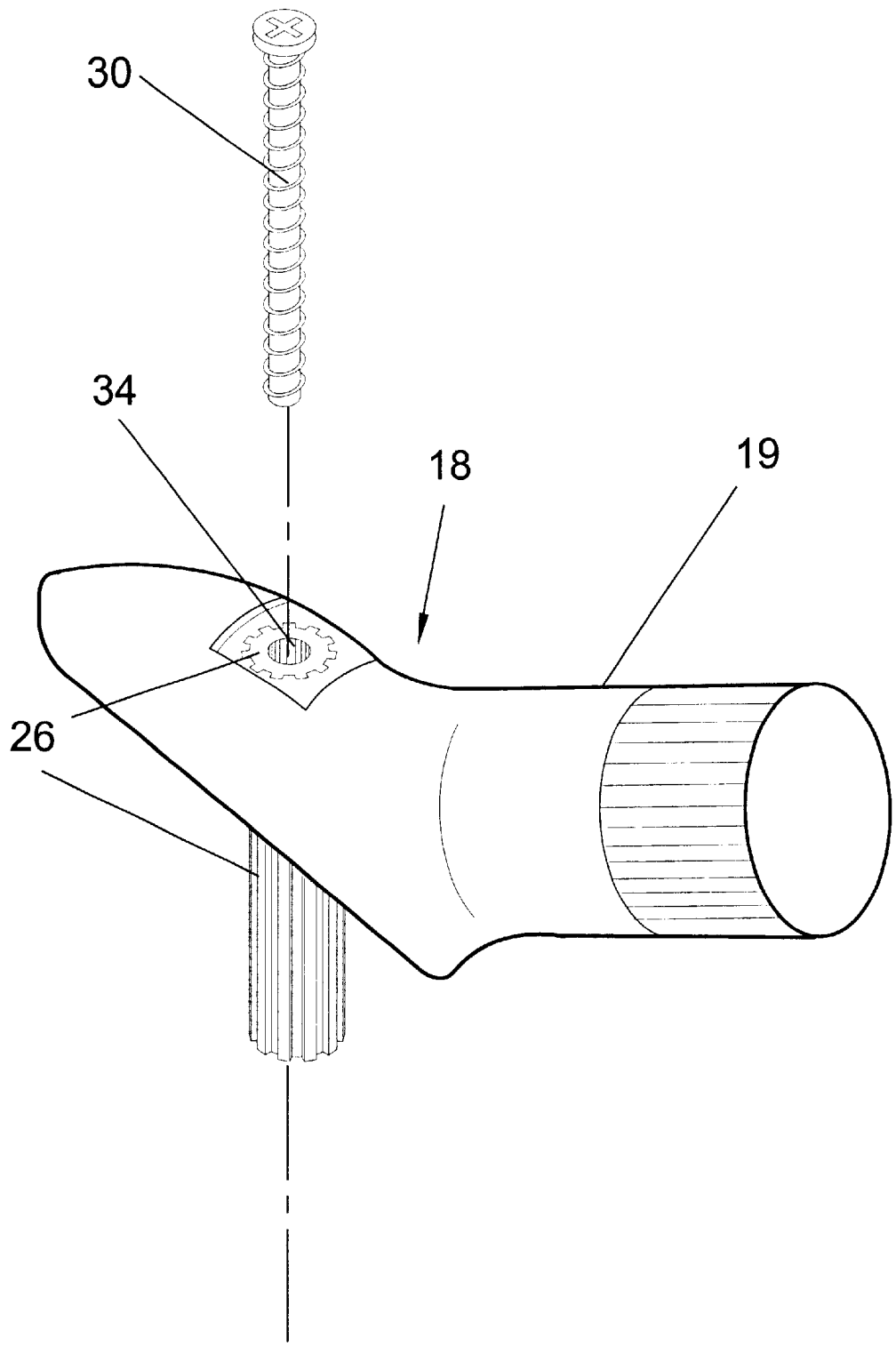
FIG. 6 is a perspective view of the neck element.

Turning to FIG. 6, shown therein is the neck element 18 with neck 19 is rotated to the desired position and the grooved shaft 26 that can be inserted into the slotted recess (not shown, see FIG. 5) with the respective slots and grooves prohibiting rotational movement thereof. The locking screw 30 is then placed into a central recess 34 extending longitudinally through the entire length of the grooved shaft and screwed into the stem element at the threaded recess (not shown, see FIG. 7).

Figure 7:
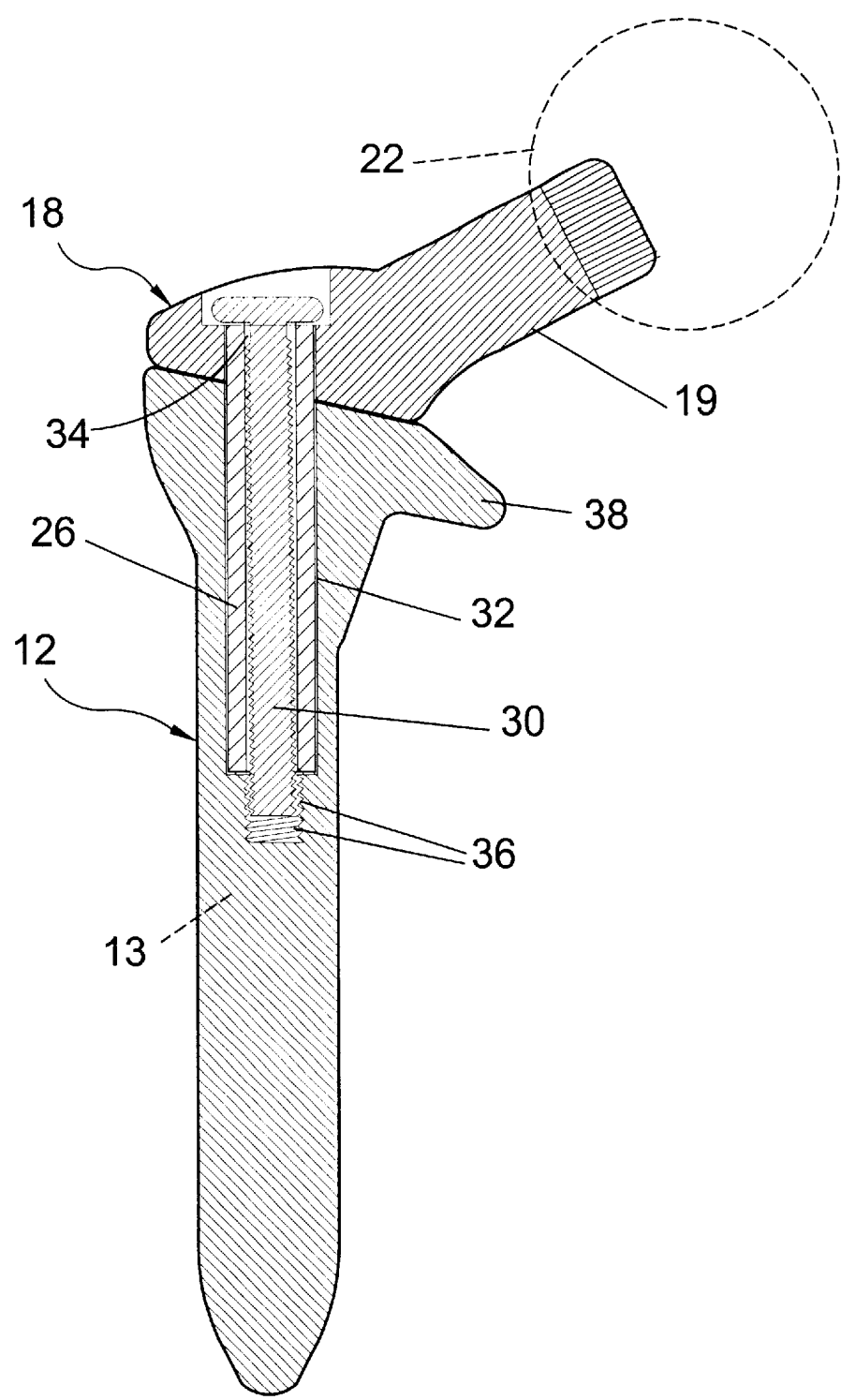
FIG. 7 is a cross sectional side view of the present invention.

Turning to FIG. 7, shown therein is the neck element 18 with neck 19 rotated to the desired position and the grooved shaft 26 inserted into the slotted recess 32 with the respective slots and grooves prohibiting rotational movement thereof. The locking screw 30 is then placed into a central recess 34 extending longitudinally through the entire length of the grooved shaft 26 and screwed into the threaded recess 36 thereafter to prevent the vertical movement thereof. Also shown is a collar-like head 38 on the upper end of stem element 12 along with the stem 13 and femoral head 22.

Figure 8:
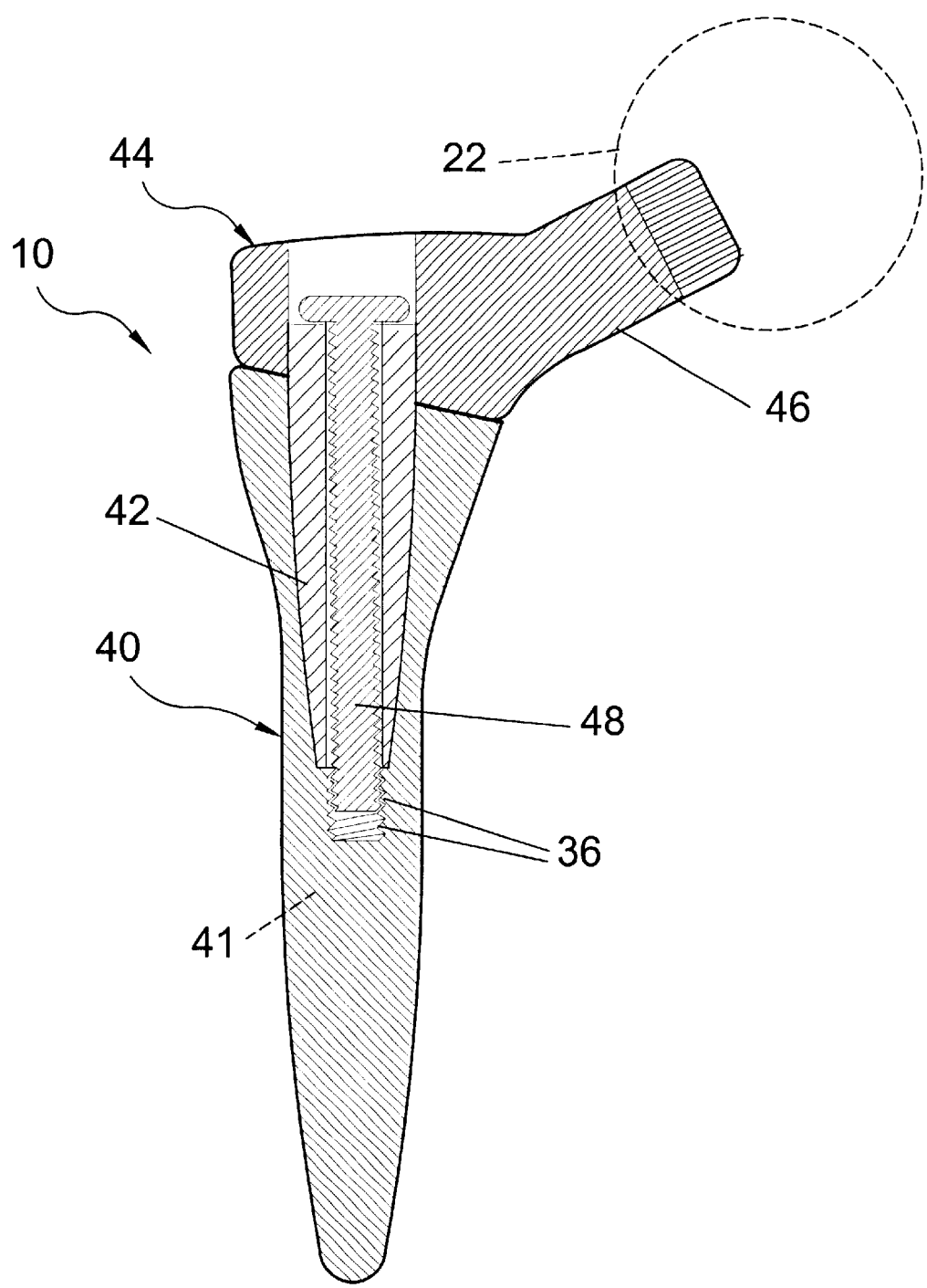
FIG. 8 is a cross sectional side view of the present invention.

Turning to FIG. 8, shown therein is a cross sectional side view of the present invention 10 having a collarless tapered stem element 40 and stem 41, a tapered grooved shaft 42 on the neck element, and a thicker neck element 44 and neck 46. Also shown is a threaded recess 36, locking means 48 and the femoral head 22.

Figure 9:
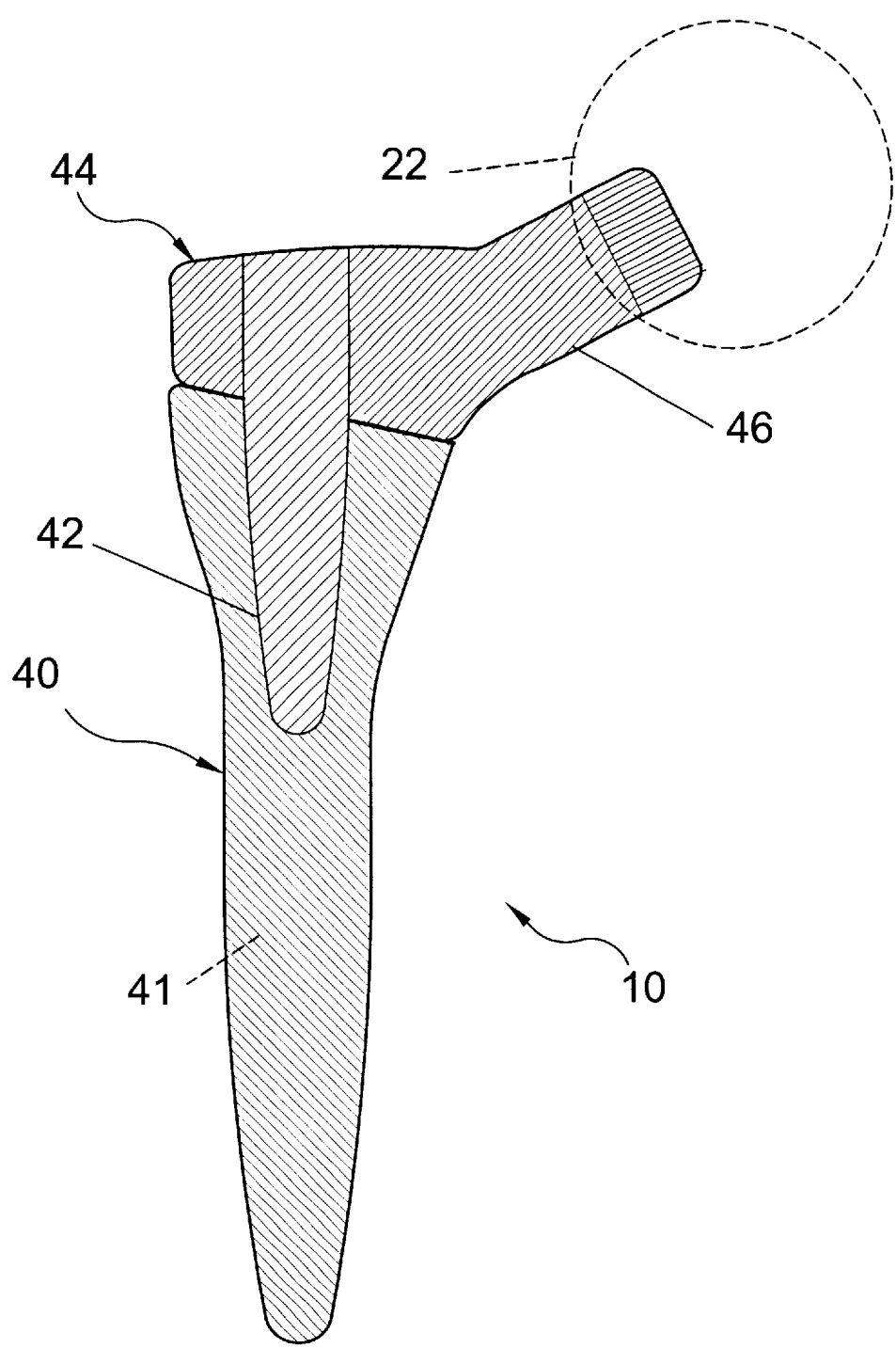
FIG. 9 is a cross sectional side view of the present invention.

Turning to FIG. 9, shown therein is a cross sectional side view of a screwless embodiment of the present invention 10 having a collarless tapered stem element 40 and stem 41, a tapered shaft 42 on a thicker neck element 44, and a neck 46. Also shown is the femoral head 22.

Figure 10:
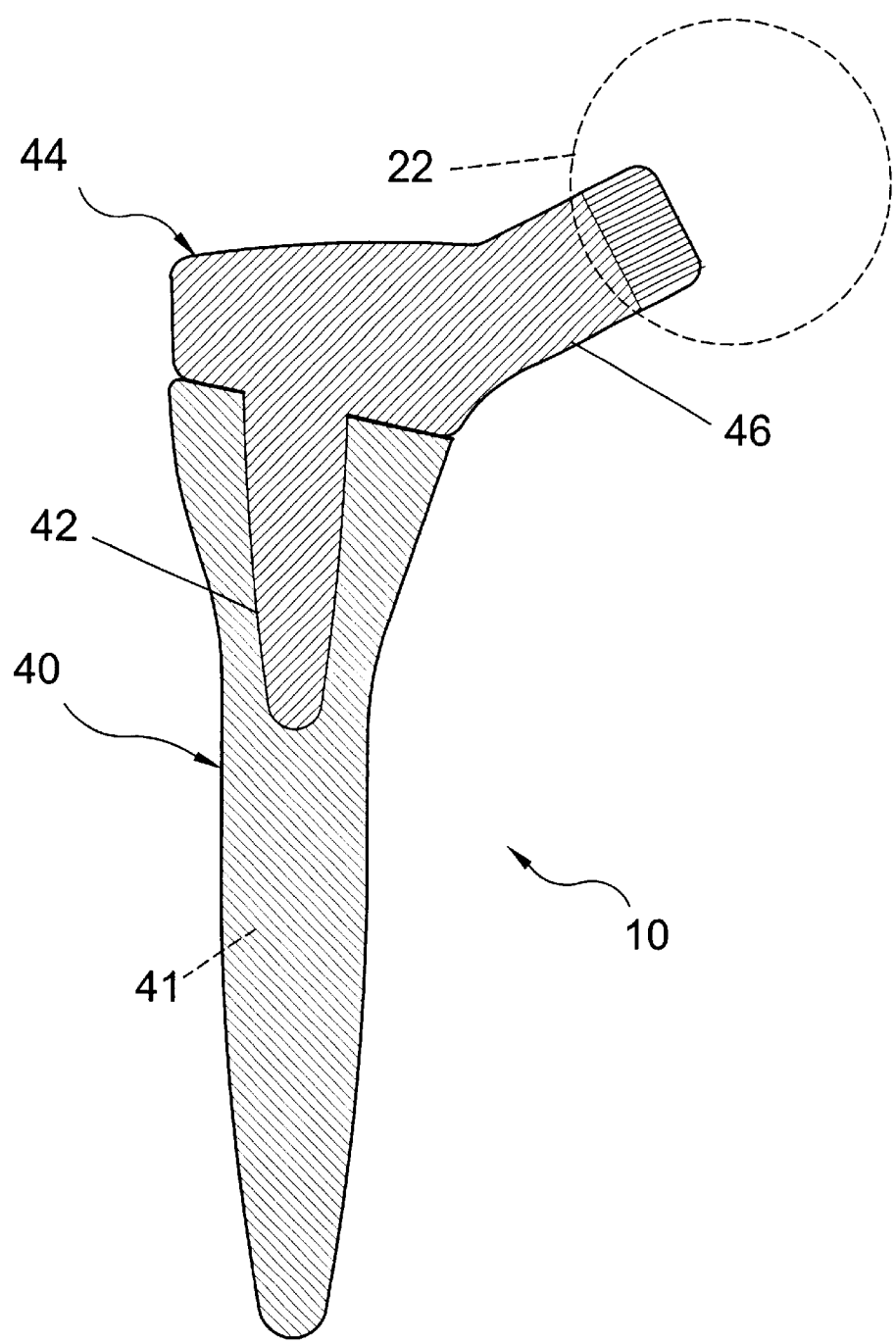
FIG. 10 is a cross sectional side view of the present invention.

Turning to FIG. 10, shown therein is a cross sectional side view of the present invention 10 having a collarless tapered stem element 40 with stem 41, a tapered grooved shaft 42 and a thicker neck element 44 with neck 46. This embodiment has the shaft 42 fabricated of the same material and from the same mold as the neck element 44 rather than having a separately manufactured shaft integral therewith. Also shown is the femoral head 22.

Figure 11:
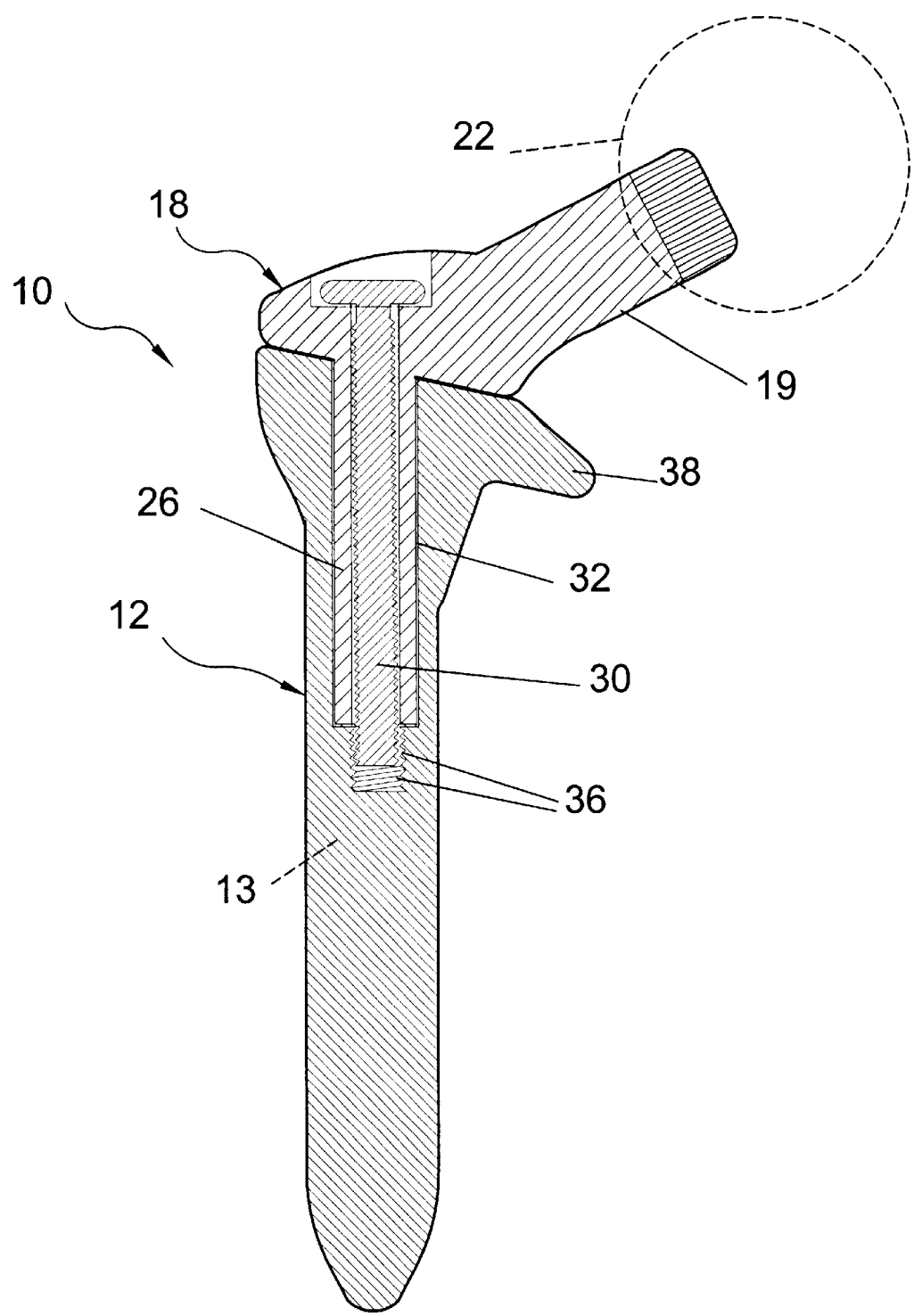
FIG. 11 is a cross sectional side view of the present invention.

Turning to FIG. 11, shown therein is a cross sectional side view of the present invention 10. This embodiment has the shaft 26 fabricated of the same material and from the same mold as the neck element 18 rather than having a separately manufactured shaft integral therewith. Other elements previously shown are also disclosed.

What is claimed to be new and desired to be protected by Letters Patent is set forth in the appended claims:

I claim:

1. An apparatus for a femoral prosthetic device for use with a conventional synthetic femoral head used with femoral components and the artificial sockets that replace the acetabulum that forms the ball and socket joint, comprising:
   a) an elongated stem element, said stem element having an upper end and a lower end;
   b) an elongated stem disposed on said lower end of said stem element, said stem for insertion into the femur;
   c) an enlarged collar disposed on said upper end of said stem element, said collar having a longitudinal recess therein;
   d) a slotted recess disposed in said longitudinal recess for receiving a grooved shaft, said recess having an upper and a lower end;
   e) a threaded recess disposed on the lower end of said slotted recess;
   f) a neck element disposed on said enlarged collar, said neck element having an underside;
   g) a neck disposed on said neck element, said neck for connection to the femoral head, said neck being offset laterally from said neck element;
   h) a grooved shaft extending through said neck element and out the underside of said neck element for insertion into and mating with said slotted recess; said grooved shaft having a central recess therein; and,
   i) a locking means for insertion into said grooved shaft, said locking means having means thereon for mating to said threaded recess to secure the neck element therein.

2. The apparatus of claim 1, wherein the grooves of said grooved shaft and the slots of said slotted recess are offset from each other by 5 to 10 degrees to allow for rotational adjustment of said neck whereby the offset and length of said neck element allows a surgeon to accommodate the needs of each patient.

3. The apparatus of claim 2, wherein said stem element has a biocompatible surface that can be gritblast for press fit applications.

4. The apparatus of claim 2, wherein said stem element has a biocompatible surface that can be porous coated for press fit applications.

5. The apparatus of claim 2, wherein said stem element has a smooth surface for cementation applications.

6. The apparatus of claim 2, wherein said locking means further comprises a locking screw for insertion into said grooved shaft and mating to said threaded recess.

7. The apparatus of claim 6, wherein said neck element and said neck are thickened.

8. The apparatus of claim 1, wherein the upper end of said stem element has a flat mating surface, the underside of said neck element has a flat mating surface, and said flat mating surfaces being flush against each other are disposed at an angle with respect to a plane perpendicular to a central axis of said slotted recess and grooved shaft.

9. An apparatus for a femoral prosthetic device for use with a conventional synthetic femoral head used with femoral components and the artificial sockets that replace the acetabulum that forms the ball and socket joint, comprising:
   a) an elongated stem element, said stem element having an upper end and a lower end, said upper end having a flat mating surface;
   b) an elongated stem disposed on said lower end of said stem element, said stem having a longitudinal recess therein, said stem for insertion into the femur;
   c) a slotted recess disposed in said longitudinal recess for receiving a grooved shaft, said recess having an upper and a lower end;
   d) a neck element disposed on said upper end of said stem element, said neck element having an underside, said underside comprising a flat mating surface adapted to mate with the stem element mating surface;
   e) a neck disposed on said neck element, said neck for connection to the femoral head, said neck being offset laterally from said neck element;
   f) said grooved shaft extending through said neck element and out the underside of said neck element for insertion into and mating with said slotted recess, the flat mating surfaces of said neck element and said stem element being at an angle with a plane perpendicular to a central axis of said slotted recess and grooved shaft; and,
   g) means for securing said grooved shaft in said slotted recess.

\* \* \* \* \*